(12) United States Patent
Wu

(10) Patent No.: US 8,415,467 B2
(45) Date of Patent: Apr. 9, 2013

(54) METHOD AND MATERIALS FOR SEPARATING NUCLEIC ACID MATERIALS

(76) Inventor: Betty Wu, Canton, MI (US)

( * ) Notice: Subject to any disclaimer, the term of this patent is extended or adjusted under 35 U.S.C. 154(b) by 191 days.

(21) Appl. No.: 12/966,056

(22) Filed: Dec. 13, 2010

(65) Prior Publication Data

US 2011/0144286 A1   Jun. 16, 2011

Related U.S. Application Data

(60) Provisional application No. 61/286,082, filed on Dec. 14, 2009.

(51) Int. Cl.
*C07H 21/00* (2006.01)

(52) U.S. Cl. .................. 536/25.4; 536/25.41; 536/25.42

(58) Field of Classification Search .......................... None
See application file for complete search history.

(56) References Cited

U.S. PATENT DOCUMENTS

| | | | |
|---|---|---|---|
| 5,898,071 A * | 4/1999 | Hawkins | 536/25.4 |
| 6,310,199 B1 | 10/2001 | Smith et al. | |
| 6,562,573 B2 | 5/2003 | Halaka | |
| 6,783,962 B1 | 8/2004 | Olander et al. | |
| 6,914,137 B2 | 7/2005 | Baker | |
| 7,319,004 B2 | 1/2008 | Harper et al. | |
| 2006/0234251 A1 | 10/2006 | Akhavan-Tafti | |
| 2009/0011469 A1 | 1/2009 | Timo | |
| 2009/0068662 A1 | 3/2009 | Hillebrand | |

OTHER PUBLICATIONS

McBain et al. Journal of Materials Chemistry (2007), vol. 17, pp. 2561-2565.*

"New isoelectric buffers for capillary electrophoresis: N-carboxymethylated polyethyleneimine as a macromolecular isoelectric buffer" Miroslav Macka,, et al; The Analyst, The Royal Society of Chemistry 2001, pp. 421-425.

* cited by examiner

*Primary Examiner* — Patrick Lewis
(74) *Attorney, Agent, or Firm* — Gifford, Krass, Sprinkle, Anderson & Citkowski, P.C.

(57) ABSTRACT

Nucleic acid material can be effectively separated from a fluid by first contacting the fluid with a positively charged polymer which binds the nucleic acid material. Thereafter, the polymer, having the nucleic acid material bonded thereto, is contacted with a releasing agent which comprises a solution of an alkaline material and a glycol. The solution has a pH of no more than 12 and operates to release the nucleic acid material from the polymer under relatively low temperature conditions, typically no more than 50° C., and in particular instances, no more than 40° C. The glycol material may comprise a monomeric glycol such as ethylene glycol, propylene glycol, or the like, or it may comprise a polymeric glycol such as polyethylene glycol. Also disclosed is a novel positively charged polymer which may be employed in the separation process. This polymer comprises an acidified polyamine, such as polyethyleneimine which has been reacted with a nonacidified polyethyleneimine in a coupling reaction. The acidified polyethyleneimine may be a coarboxylated and/or sulfonated polyethyleneimine.

13 Claims, No Drawings

METHOD AND MATERIALS FOR SEPARATING NUCLEIC ACID MATERIALS

CROSS-REFERENCE TO RELATED APPLICATION

This application claims priority of U.S. Provisional Patent Application Ser. No. 61/286,082 filed Dec. 14, 2009, and entitled "Method and Materials for Separating Nucleic Acid Materials", the disclosure of which is incorporated herein by reference.

FIELD OF THE INVENTION

This invention relates to the separation of nucleic acid materials from various sample materials such as whole blood, serum, plasma, solid tissue, body fluids, tissues, hair, nail material, buccal cells, cultured cells, vaginal swabs, bacteria, fungus, and plant tissue. More specifically, the invention relates to methods and materials which allow for the efficient and rapid separation of nucleic acid materials under mild temperature and pH conditions.

BACKGROUND OF THE INVENTION

It is often necessary to separate synthetic and naturally occurring nucleic acid materials such as DNA, RNA, oligonucleotides, and the like from various biological samples and other fluids such as cell lysates, synthetic reaction mixtures, PCR reaction mixtures, and the like. Such separations can be very important steps in various analytical procedures, synthetic procedures, and research activities. Any such method should be reliable, efficient, easy to implement, and not destructive of the nucleic acid materials.

In many instances, positively charged polymers such as polylysine and polyethyleneimine based materials have been used in gene delivery and various nucleic acid purification processes, since these types of molecules can effectively capture and retain negatively charged nucleic acid materials. In such processes, the charged polymers are typically immobilized on a solid surface, such as a magnetic particle, polystyrene particles or the like. The charged polymer is then contacted with a sample containing a nucleic acid material typically at a pH of less than 8. This causes the nucleic acid material to bind to the positively charged polymer. Impurities such as proteins and carbohydrates do not bind and can be washed away from the sample. The bound nucleic acid material is then released from the polymer under high pH conditions so as to achieve purification. However, in many instances the nucleic acid materials bind very strongly to the polymer thereby requiring use of high pH and high temperature conditions to release the bound nucleic acid from the polymer. However, the nucleic acid materials can be permanently denatured by such high temperature and alkaline reaction conditions. Therefore, there is a need for methods and materials which allow for the separation and purification of nucleic acid materials under relatively mild pH and temperature conditions. As will be explained in detail hereinbelow, the present invention allows for the binding, separation, and release of nucleic acid materials at room temperature and under mildly alkaline conditions. These and other advantages of the invention will be apparent from the discussion and description which follow.

BRIEF DESCRIPTION OF THE INVENTION

Disclosed is a method for separating nucleic acid material from biological samples or other fluid mixtures. According to the method, the sample, having the nucleic acid material therein is, in the instance where it includes intact cells first lysed with lysis buffer to release nucleic acid material; in samples which do not include intact cells, this step may be omitted. Subsequently, the fluid is contacted with a positively charged polymer, such as polylysine, polyethyleneimine, or other such polyamines used either singly or in combination. The unbound impurities are washed away with a washing buffer. The positively charged polymer binds the nucleic acid material thereto; and in a second step of the invention, the polymer having the nucleic acid material bonded thereto is contacted with a releasing agent which comprises a solution of an alkaline material and a glycol. The solution has a pH of no more than 12, and the solution is effective to cause the nucleic acid material to be released from the polymer. The releasing solution may further include a buffer, and in particular instances, the solution has a pH of no more than 11. The alkaline material may comprise a group I metal hydroxide such as sodium hydroxide or potassium hydroxide, and the concentration of the alkaline material may be, in some instances, no more than 50 mM.

The glycol, in some instances, is a polymeric glycol such as polyethylene glycol, and may have a molecular weight in the range of 200-2000. The step of contacting the polymer with a releasing agent is, in particular instances, carried out at temperatures of no more than 40° C.

In some instances, the positively charged polymer is a carboxylated polyamine. The positively charged polymer may comprise all or a portion of a matrix configured as beads, sheets, slides, tubes, pipettes, swabs, magnetic particles, and the like. The method of the present invention may be implemented in an automated system or on a manual basis.

Further disclosed is a method for preparing a partially positively charged polyethyleneimine polymer. According to the method, a polyethyleneimine polymer is reacted with an acidifying agent, such as a carboxylating agent or a sulfonating agent, so as to produce an acidified polyethyleneimine and that acidified polyethyleneimine is then reacted with a second volume of a polyethyleneimine so as to couple at least some of the acidified polyethyleneimine to the polyethyleneimine of the second volume. In particular instances, the acidifying agent is a carboxylating agent which may be sodium chloroacetate.

Further disclosed is a system for carrying out the method of the present invention as well as a kit of parts for carrying out the method of the invention.

DETAILED DESCRIPTION OF THE INVENTION

According to the present invention, nucleic acid materials which have been bound to separation reagents such as positively charged polymers are released therefrom by contacting them with a releasing reagent which includes an alkaline material and a glycol. The releasing solution has a pH of no more than 12, and in some instances no more than 11. This solution is effective to release nucleic acid materials at relatively low temperatures, such as temperatures of no more than 50° C. In particular instances, release of the nucleic acid materials takes place at room temperature, which is generally understood to be a temperature of no more than 40° C. Typically, the release is accomplished in no more than 10 minutes, and in particular instances no more than 5 minutes. These mild conditions avoid, or greatly minimize, damage to the nucleic acid materials.

In specific instances, the alkaline material in the releasing agent is a group I metal hydroxide such as sodium hydroxide, potassium hydroxide, or the like. The glycol material may comprise ethylene glycol; however, in some specific instances, it has been found that polymeric glycol materials such as polyethylene glycol polymers are very effective in the practice of the present invention. In specific instances, the concentration of the alkali material is less than 50 mM and the concentration of the glycol component, on a weight basis, is in the range of 1-40%. In particular instances, the molecular weight of the polyethylene glycol polymers can range from 200 to 2000.

One specific reagent having utility in the practice of the present invention comprises an approximately 8 mM aqueous solution of sodium hydroxide containing approximately 30% by weight of polyethylene glycol (PEG 600). Other similar compositions will be readily apparent to those of skill in the art. It has been found that compositions of this type generally have a pH of no more than 12, and typically no more than 11, and these compositions have been shown to efficiently release nucleic acid materials from positively charged polymers such as carboxylated polyethyleneimine (PEI) at temperatures of no more than 50° C., and typically no more than 40° C. (room temperature) within 4 or 5 minutes. These mild pH and temperature conditions minimize damage to the nucleic acid materials. It is to be understood that the releasing reagent may include further ingredients such as buffers which operate to maintain an appropriate pH level, surfactants, as well as ancillary ingredients such as viscosity control agents and the like.

The positively charged polymers used in the present invention may comprise a bulk polymeric material, or they may comprise coatings on substrates such as beads, particles, strips, slides, tubes, or pipettes. The substrates may also comprise bibulous materials such as swabs, sponges, or the like. In some instances, the positively charged polymeric material may be prepared by derivatizing, grafting, or otherwise modifying a bulk polymeric body. In some cases, the positively charged polymer is coated onto a magnetic particle, or a magnetically susceptible particle, so as to facilitate collection of the particles by magnetic means.

A series of experiments illustrating the principles of the present invention were carried out. In a first experiment, a DNA sample was absorbed onto PEI modified magnetic particles of the type known in the art for use in the separation of nucleic acid materials. In this regard, the PEI modified magnetic particles were first incubated with a 200 ng sample of purified mouse genomic DNA in 30 microliters of a buffer solution comprising 50 mM Tris-HCl having a pH of 7.5 and further containing 1% of Triton X-100. Incubation was carried out at room temperature for 2 minutes. A series of tubes containing the samples were placed in a magnetic separator and the supernatant was removed carefully with a pipette leaving the particles behind. The bound DNA was released from the particles. In a first instance the release was carried out utilizing a prior art reagent solution comprising 10 microliters of 20 mM NaOH. In a second instance, the releasing reagent comprised a mixture of 8 mM NaOH and 30% PEG 600, in accord with the present invention. In either instance, incubation was carried out at room temperature for 4 minutes. The resultant solutions were neutralized with 10 microliters of 100 mM Tris-HCl, pH 8.0. A portion of each sample was then analyzed via agarose gel electrophoresis. The electrophoresis analysis indicated that the 8 mM NaOH/PEG solution of the present invention efficiently liberated the DNA from the PEI polymer at room temperature conditions, while the prior art high pH solution did not.

In a second experimental series, frozen human peripheral blood was first lysed in 75 microliters of a lysis buffer consisting of 50 mM Tris-HCl, pH 7.5 buffer, containing 100 mM KCl, 1% Triton X-100, and 0.5% SDS. Lysis was carried out for 2 minutes at room temperature. PEI modified magnetic particles (10 microliters, 1.6% v/v) were added to lysate to bind the released DNA. The bound DNA was collected by placing the tubes into a magnetic separator for 2 minutes. Cell debris in the supernatant was removed, and the magnetic particles having the DNA bound thereto were incubated with 200 microliters of a washing buffer containing 20 mM Tris-HCl, pH 8.0, 0.5% SDS and 200 microgram of proteinase K, for 10 minutes at 60° C. The magnetic particles were then washed with the same buffer solution, not including the proteinase K. After, the particles were washed with 200 microliters of a solution containing 10 mM Tris pH 8.0. The DNA was then released in 16 microliters of a releasing solution of the present invention containing 8 mM NaOH and 30% PEG 600 at room temperature for 4 minutes. The released DNA was then neutralized with 4 microliters of a 100 mM Tris-HCl, pH 8.0 buffer. A comparison was carried out utilizing a releasing agent comprising a prior art, glycol-free 20 mM NaOH solution. As in Experiment 1, the resultant materials were analyzed by gel electrophoresis, and this experiment demonstrated that the solution of the present invention was highly effective in releasing the bound DNA, while the prior art solution was not.

A further experimental series was carried out demonstrating the effectiveness of the composition of the present invention for releasing bound RNA. In this experiment, approximately $4 \times 10^6$ 293 cells were quickly harvested from a 10 centimeter tissue culture plate by centrifugation. The supernatant liquid was discarded, and the cell pellet was stored at $-80°$ C. prior to use. In order to isolate the RNA, 400 microliters of a lysis buffer (25 mM Na citrate, 4 M guanidine isothiocyanate, 5 mM EDTA, 2% TX-100) was added to the frozen cell pellet. After mixing, 20 microliters of PEI magnetic beads were added to the lysis buffer and mixed. A sample tube containing the mixture was placed on a magnetic rack so as to form a pellet of the magnetic beads. The supernatant liquid was discarded and the beads were washed once with 400 microliters of a washing buffer (2 mM Na citrate, pH 6.0) and then incubated with 100 microliters of DNase I solution (40 mM Tris, pH 7.5, 8 mM $MgCl_2$, 5 mM DTT and 50 units of DNase I) at 37° C. for 15 minutes. The beads were then washed twice with the washing buffer after the DNase I treatment. The bound RNA was then released from the beads with 60 microliters of a release buffer comprising 0.1 M Bis-Tris, pH 9.5 and 30% PEG 600. 10 microliters of the released RNA was used for cDNA synthesis with M-MLV reverse transcriptase obtained from Takara Bio Inc. 2 microliters of the synthesized cDNA from the 50 microliter reaction were used for PCR with primers for human beta-actin cDNA. The cDNA thus prepared was analyzed by gel electrophoresis in comparison with a control sample. The analysis confirmed that the releasing agent of the present invention was highly effective in freeing the RNA from the magnetic particles.

In a fourth experiment, a novel, positively charged PEI material was prepared in accord with another aspect of the present invention. In a first step of the process, a sodium chloroacetate carboxylating agent was used to carboxylate a sample of PEI material (MW 200,000). This process was carried out by a method described by Miroslav Macka et al. "New isoelectric buffers for capillary electrophoresis: N-carboxymethylated polyethyleneimine as a macromolecular isoelectric buffer," *Analyst*, 2001, 126, 421-425. Thereafter, 100 mg of the thus-prepared carboxylated PEI was dissolved in 1 milliliter of ethanol, and various volumes ranging from 10-50 microliters of carboxylated PEI were added to 100 microliters of PEI magnetic particles in 50 mM MES buffer, pH 6.1, containing carbodiimide and N-hydroxysuccinimide. The magnetic particles thus prepared were shaken for 2 hours at room temperature. Thereafter, the samples were placed in a magnetic separator and any uncoupled carboxylated PEI was removed. The magnetic particles thus produced were washed twice with 50 mM MES and stored in 100 microliters of 50 mM MES plus 0.1% Triton X-100. It is to be understood that this method may be used to prepare other types of positively charged (acidified) polymers. For example, the PEI could be reacted with a sulfonating reagent so as to produce a sulfonated PEI, which is then coupled with a volume of unsulfonated PEI.

In a subsequent experiment, the thus-prepared carboxylated PEI magnetic particles were utilized to capture DNA. In this regard, the binding capacity of various carboxylated PEI magnetic particles were tested with 200-500 nanograms of purified mouse genomic DNA, in a process generally similar to that described with reference to Example 1. In this regard, supernatants were collected after incubation of the DNA with the carboxylated PEI magnetic particles in 30 microliters of a buffer containing 50 mM Tris-HCl, pH 7.5 and 1% Triton X-100, under room temperature conditions for 2 minutes. The bound DNA was released utilizing a reagent in accord with the present invention comprising 8 mM NaOH and 30% PEG 600, under room temperature conditions. Both bound and unbound DNA were visualized on a 0.8% agarose gel utilizing ethidium bromide staining. It was found that the carboxylated PEI magnetic particle material left no DNA in the supernatant, demonstrating the effectiveness of this novel carboxylated material as a positively charged polymer for the separation of nucleic acid materials.

In a subsequent experiment, various releasing solutions were evaluated for their efficacy in releasing DNA from the carboxylated PEI material of the present invention and from prior art noncarboxylated PEI. It was found that if the polymer was not carboxylated, release was somewhat more difficult. Specifically, it was found that, with regard to the non-carboxylated PEI polymer, a composition of sodium hydroxide and PEG 600 (pH 11-12) was required to give greater than 90% recovery of bound DNA, while milder (lower pH) releasing agents, such as a 100 mM Bis-Tris, pH 9.0 solution, were not as effective. In those instances where the carboxylated PEI polymer was employed, it was found that a releasing agent comprising the 100 mM Bis-Tris, pH 9.0 solution can effectively bring about release of approximately 90% of the DNA at room temperature.

In a further experiment, RNA was separated utilizing the carboxylated PEI polymer. In this regard, RNA was extracted from Cos7 cells. And 500 nanograms of the extracted RNA was then incubated with the carboxylated PEI magnetic particles at room temperature for 2 minutes. The bound RNA was then released utilizing, in one instance, a Bis-Tris pH 9.0 buffer, and in another instance the same Bis-Tris buffer with polyethylene glycol. The releasing was carried out 42° C. for 3 minutes. The thus-released RNA was subject to quantitative SYBR green PCR with primers specifically to monkey cyclophilin A. It was found that the addition of the PEG to the buffer improves RNA recovery significantly.

The foregoing illustrates some embodiments of the present invention. Other embodiments and modifications thereof will be readily apparent to those of skill in the art in view of the teaching presented herein. For example, the releasing agents of the present invention may be prepared utilizing alkali materials other than the described sodium hydroxide. Likewise, other glycol materials including polymeric and oligomeric glycols, as well as monomeric glycols, may be used in the practice of the present invention. Also, it is to be understood that the present invention may be implemented in automated as well as manual modes. And, in accord with the present invention, kits for carrying out the method may be prepared. All of such modifications and variations are within the scope of the present invention. It is the following claims, including all equivalents, which define the invention.

The invention claimed is:

1. A method for separating nucleic acid material from a fluid, said method comprising the steps of:
    contacting a fluid having a nucleic acid material therein with a positively charged polymer whereby said nucleic acid material binds to said positively charged polymer; and
    contacting said polymer having said nucleic acid material bonded thereto with a releasing agent, said releasing agent comprising a solution of an alkaline material and a glycol, said solution having a pH of no more than 12, whereby said agent causes said nucleic acid material to be released from said polymer.

2. The method of claim 1, wherein said agent has a pH of no more than 11.

3. The method of claim 1, wherein said agent includes a buffer.

4. The method of claim 1, wherein said alkaline material is a group I metal hydroxide.

5. The method of claim 1, wherein said alkaline material is present in a concentration no more than 50 mM.

6. The method of claim 1, wherein said glycol is a polymeric glycol.

7. The method of claim 6, wherein said polymeric glycol is polyethylene glycol.

8. The method of claim 7, wherein said polyethylene glycol has a molecular weight in the range of 200-2000.

9. The method of claim 1, wherein said step of contacting said polymer with said releasing agent is carried out at a temperature of no more than 40° C.

10. The method of claim 1, wherein said step of contacting said fluid with said polymer is carried out for no more than 10 minutes.

11. The method of claim 1, wherein said positively charged polymer includes a member selected from the group consisting of polyamines.

12. The method of claim 1, wherein said positively charged polymer is a carboxylated polyamine.

13. The method of claim 1, wherein said positively charged polymer is part of a matrix comprising one or more of: beads, sheets, slides, tubes, pipettes, swabs, and magnetic particles.

* * * * *